United States Patent [19]

McCloskey et al.

[11] 4,248,785

[45] Feb. 3, 1981

[54] PREPARATION OF GERMAAZASPIRODIONES AND GERMAAZASPIRANES

[75] Inventors: Chester M. McCloskey, Altadena; James R. Fischer, Claremont; Leonard F. Scott, Long Beach, all of Calif.

[73] Assignee: The Norac Company, Inc., Azusa, Calif.

[21] Appl. No.: 33,429

[22] Filed: Apr. 26, 1979

[51] Int. Cl.$^3$ ............... C07D 207/40; C07D 295/12
[52] U.S. Cl. ........................ 260/326.5 A; 260/326.9
[58] Field of Search ................. 260/326.5 A, 326.9

[56] References Cited

U.S. PATENT DOCUMENTS 3,825,546   7/1974   Rice .................................. 260/293.66

OTHER PUBLICATIONS

Rice et al., J. Heterocyclic Chem. 11, pp. 1041–1047, (1974).

*Primary Examiner*—Jose Tovar
*Attorney, Agent, or Firm*—Keil & Witherspoon

[57] ABSTRACT

Novel high purity crystalline forms of dialkylgermaazaspirodiones, their preparation and their use in an improved process for the preparation of high purity dialkylgermaazaspiranes and their acid addition salts is disclosed.

26 Claims, No Drawings

PREPARATION OF GERMAAZASPIRODIONES AND GERMAAZASPIRANES

This invention involves the discovery of novel crystalline forms of lower-alkyl germaazaspirodiones and thereby a simple method for preparing very pure di-lower-alkylgermaazaspirodiones of the formula:

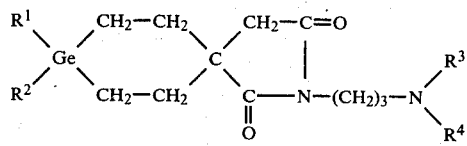

wherein: $R^1$ and $R^2$ are the same or different alkyl groups of 1 to about 4 carbon atoms, and $R^3$ and $R^4$ are the same or different alkyl groups of 1 to about 4 carbon atoms.

This invention further relates to an improved process for the preparation of the lower-alkyl germaazaspiranes and their acid addition salts employing the highly purified dialkylgermaazaspirodiones.

The dialkylgermaazaspiranes are physiologically active, with antineoplastic properties. As pharmaceutical compounds, the dialkylgermaazaspiranes and their acid-addition salts are required in high purity.

Dialkylgermaazaspirodiones and dialkylgermaazaspiranes were synthesized by Rice, Wheeler and Geschickter as described in J. Heterocyclic Chem., 11, 1041 (1974) and in U.S. Pat. No. 3,825,546 to Rice.

In their process, Rice, Wheeler and Geschickter (unlike one silicone analogue which was crystalline) obtained the dialkylgermaazaspirodiones (from which the dialkylgermaazaspiranes were prepared) as liquids and purified them by distillation. The germaazadiones were reduced to the germaazaspiranes (also as liquids) which were also purified by distillation and finally converted to the crystalline acid addition salts. Due to the high molecular weights of both the dialkylgermaazaspirodiones and the spiranes, purification by distillation is difficult and inefficient, especially on a commercial scale, due to the inherent difficulties of fractional distillation at the high temperatures and very low pressures required. Purification by crystallization of the dialkylgermaazaspirane acid salts, particularly the hydrochloride, is not an efficient purification procedure since these salts crystallize in exceedingly fine crystals that are difficult to filter and wash, and several of the common impurities tend to co-crystallize with the desired products. This procedure is also wasteful in yield, particularly when recrystallization is required.

In order to simplify somewhat the problems of purification of the diones and spiranes, Rice, Wheeler and Geschickter utilized highly purified diacids to prepare the anhydrides which are the immediate precursors of the diones. Purification at the diacid stage, however, is difficult and inefficient.

The present discovery came about as follows. Some diethylgermaazaspirodione (N-(3-dimethylaminopropyl)-2-aza -8,8-diethyl-8-germaspiro[4:5]decane-1,3-dione) had been prepared by the method of Rice, Wheeler and Geschickter. It had been purified by distillation and was found to remain a liquid over a period of several months, similar to the experience reported by Rice, Wheeler and Geschickter. After working with this dione in normal laboratory testing for over a month, a small crystalline mass about the size of a pea unexpectedly was seen to have developed on the surface of the thick liquid dione in one of several 500 g. lots. It is not known what initiated the crystal formation. Perhaps it was initiated by a particle of dust of just the right structure. In any event, the crystalline mass was removed and slurried with a small amount of pentane, and the crystals were isolated by filtration. Once these crystals were obtained, crystallization of additional diethylgermaazaspirodione was easily initiated by utilizing the first formed crystals as seed crystals. (Crystallization thereafter occasionally occurred without seeding, presumably due to seed crystals in the atmosphere.)

The diethylgermaazaspirodione unexpectedly was found to crystallize in large orthorhombic crystals of very high purity, which are easily separated from the mother liquor by techniques such as centrifuging, filtering or decanting. The crystalline product is obtained in an exceptional purity unobtainable by any other known manufacturing procedure. Centrifugation of the neat crude crystalline material yields a product of 95% purity or over, and with a small amount of solvent and washing a purity of 98% is obtained. Crystallization from a solvent unexpectedly gave a product with a purity of 99% or over, while by recrystallization from a solvent the purity can be raised to at least 99.8%.

The melting point of the pure diethylgermaazaspirodione is best determined by the freezing point method and was found to be 41.88° C. The dialkylgermaazaspirodiones have significant heats of crystallization and the freezing point is depressed by minute amounts of impurities so that the freezing point is an accurate and sensitive index of purity. By crystallization, recovery of residual product from the mother liquors is readily carried out, as is recrystallization, to give a high overall yield of highly purified dione.

An important added advantage of purifying the diones by crystallization is that the diacid and anhydride precursors do not have to be highly purified, as is required when purification of the diones by distillation is employed. This is of particular importance in commercial preparations since the overall processing is greatly simplified while at the same time higher overall yields are obtained.

Purification of the diones by crystallization is commonly carried out in the presence of a solvent. Common organic solvents can be employed provided they are not reactive. Those that are volatile enough to be removed by evaporation and in which the diones have the lowest solubility are preferred. However, the diones are very soluble in most solvents so that low temperatures may be required, or are desirable, for efficient processing. Low boiling hydrocarbons such as pentane, hexane, heptane or petroleum ether are particularly useful solvents in this process. Fluorocarbons, flurochlorocarbons and ethers are also practical solvents.

While solvents are commonly employed, in those instances where the dione contains relatively high levels of impurities, solvents may not be required initially. In such instances, the crystallization may be carried out by seeding the impure mixture, allowing the crystals of the dialkylgermaazaspirodione to form and separating them from the noncrystalline phase. Recrystallization of the dione so obtained from a solvent may be carried out to remove the last traces of impurities.

In the preferred method, the crystallization process is carried out by mixing the liquid dione with a low boiling hydrocarbon solvent or by dissolving crystalline material in such a solvent by warming. The solution so obtained is then cooled to a temperature at which crystallization can occur. This temperature varies with the solvent and the concentration, but is usually 10°–15° below the freezing point of the dione. The solution is seeded and the crystallization is allowed to proceed with or without stirring while cooling slowly. After the crystallizing mixture has been at the final temperature for several hours, usually room temperature or refrigerated temperatures (−6° to +6° C. for the diethyl compound with pentane or hexane), the crystals are separated, such as by filtering or centrifuging, and then washed with a small amount of solvent (preferably cold). If mechanical or frequent stirring is not employed during crystallization, the removal of the crystals in two stages such as at room temperature and then after refrigeration can be advantageous. After separation of the crystals, the remaining solvent can be removed by standard drying techniques.

Once the procedure has been carried out, seed crystals may not be required to initiate crystallation.

Crystallization of the dione from crude liquor may be slow and require a prolonged period of time to obtain the maximum yield and optimum crystal size. Low temperatures may be employed to maximize yield.

It has been further discovered that the highly purified dialkylgermaazaspirodiones, obtained by crystallization, can be reduced to dialkylgermaazaspiranes which do not require distillation or purification, but rather can be converted directly to the acid-addition compounds in exceptional overall yield and purity. The overall yield of quality product for both of these reaction steps approaches quantitative, when the mother liquors are reworked. The yields are usually in the range of 98% and seldom fall below 95%. In addition to the chloride, other acids with pharmaceutically acceptable, non-toxic anions may be employed, such as those having as anions: iodide, acetate, bromide, sulfate, perchlorate, mucate, fumarate, succinate, citrate and phosphate, which are soluble in water or other well-tolerated solvents.

Reduction of the dione is carried out by use of lithium aluminum hydride or other highly efficient reducing agents for carbonyl groups that do not rupture the carbon-nitrogen bond. The process can also be carried out catalytically.

While the acid addition compound can be prepared from the neat dialkylgermaazaspirane, provided suitable means are employed to prevent overheating, the preparation of the acid addition salt is normally carried out in the presence of a solvent. Solvents from which the acid-addition salt can be crystallized and in which trace impurities are soluble are preferred. Alcohols such as methyl, ehtyl, propyl, isopropyl and mixture thereof are particularly useful, especially with hydrogen chloride addition salts. Commonly, the acid is added to a solution of the germaazaspirane in the solvent or as a solution of the acid in the solvent. Slow crystallization of the acid-addition salt from the solvent is often desirable to obtain optimum crystal size for efficient filtration, washing, and thus higher purity.

The instant invention applies to those compounds in which the "lower alkyl" groups attached to the germanium atom contain 1 to about 4 carbon atoms. The alkyl groups are commonly the same, but may be different. Similarly, the "lower alkyl" groups attached to the nitrogen atom contain 1 to about 4 carbon atoms and may be the same or different. The preferred form is that in which the alkyl groups contain 1 to 4 carbon atoms. The most preferred form is that in which the alkyl groups attached to the germanium atom are ethyl and the alkyl groups attached to the nitrogen atom are methyl.

The term "lower alkyl" as used herein refers to alkyl groups containing 1 to about 4 carbon atoms.

The invention will be further described by reference to the following examples, which set forth specific embodiments of the present invention. These embodiments, however, are merely illustrative and are not to be construed as limitative of the present invention.

EXAMPLE 1

Purification of a Distilled Diethylgermaazaspriodine by Crystallization

N-(3-dimethylaminopropyl)-2-aza-8,8-diethyl-8-germaspiro[4:5]decane-1,3-dione, 216 g, a viscous liquid obtained by distillation (b.p. 147°–153° C.; 0.1 mm; purity: 90% by gas chromatography) prepared from anhydride (m.p. 47.5° C.; purity: 81% by gas chromatography) according to the procedure of Rice, Wheeler & Geschickter, was dissolved in 85 ml (53.5 g) of pentane. The solution was seeded and stirred mechanically for 12 hours while cooling to 6° C. The crystals were separated by centrifuging (through a porous filter) and washed with a small amount of cold pentane with centrifuging. Yield: 162 g, f.p. 40.2° C. (purity: 99% by gas chromatography). The mother liquor and washings were saved for reclamation.

EXAMPLE 2

Purification of a Diethylgermaazaspirodione by Recrystallization

I. Two-Stage Recrystallization

N-(3-dimethylaminopropyl)-2-aza-8,8-diethyl-8-germaspiro[4:5]decane-1,3-dione (f.p. 41.3° C.), 1660 g, was dissolved in 500 g of warm hexane. The solution was cooled to 27° C. and a seed crystal added. Crystallization was allowed to proceed for 2 hours with occasional stirring while the temperature was cooled to 23° C. The crystals were removed by filtration, washed with 300 ml of cold hexane and vacuum dried. Yield 857 g, f.p. 41.84° C. (purity: 99.8+% by gas chromatography). The filtrate was cooled to 7° C. overnight and the crystals that formed were removed by filtration and washed with 200 ml of hexane (6° C.) and vacuum dried. Yield: 528 g, f.p. 41.50° C. The filtrates and washings were saved for recovery of the dione contained therein.

II. Use of Isopropyl Ether

Another lot of 71 g of diethylgermaazaspirodione, with a freezing point of 41.85° C., was dissolved in 21 g of freshly distilled isopropyl ether by warming. On cooling to 25° C., seeding and cooling to 20° C., and after filtering and washing, there was obtained 55 g of dione (f.p. 41.88° C.) as the first crop of crystals.

III. Recrystallization of Low-Quality Dione

Another lot of 400 g of diethylgermaazaspirodione with a freezing point of 40° C. was dissolved in 100 g pentane by warming in a 40° C. water bath. The solution was cooled to room temperature, seeded, then placed in a refrigerator for 24 hours at 8° C. The resulting crystalline mass was broken up with a spatula, and then centrifuged free of mother liquor. The damp crystals were washed with 50 ml pentane at 0° C. and then air-dried to give 345 g (f.p. 41.6° C.) of dione as the first crop.

EXAMPLE 3

Preparation of a Diethylgermaazaspirodione Without Distillation

Crude N-(3-dimethylaminopropyl)-2-aza-8,8-diethyl-8-germaspiro[4:5]decane-1,3-dione, prepared according to the method of Rice, Wheeler & Geschickter from 285 g anhydride having a freezing point of 57° C., was dissolved in 1200 ml of pentane, washed twice with 150 ml of water, dried over sodium sulfate and filtered. The solution was concentrated to 500 ml, cooled to room temperature and seeded. After 3 hours with occasional stirring, the solution was placed in a refrigerator and maintained at 3° C. overnight. The crystals were filtered off, washed with 25 ml of cold pentane and dried to give 301 g of product having a slight yellow color and a freezing point of 41.5° C. The filtrate was concentrated to 70 ml and cooled. There was obtained 15 g of additional dione (f.p. 41.0° C.). The mother liquors were saved for reclamation.

EXAMPLE 4

Preparation of N-(3-Dimethylaminopropyl)-2-aza-8,8-diethyl-8-germaspiro[4:5]decane Dihydrochloride I. Dione Reduction Eight liters of anhydrous ethyl ether and 339 g of powdered lithium aluminum hydride were stirred for 1 hour. A solution of 2200 g N-(3-dimethylaminopropyl)-2-aza-8,8-diethyl-8-germaspiro[4:5]decane-1,3-dione (f.p. 41.7° C.) in 5 liters of anhydrous ethyl ether was then added over a period of 1.25 hr. Stirring was continued for 3 hours after the dione addition was completed.

Unreacted LiAlH$_4$ was decomposed by adding 1100 ml water slowly, with stirring. Stirring was continued for 0.5 hr. and the mixture was then allowed to stand for 3 hours. The solids were filtered out and washed with 8 liters of ethyl ether. The filtrate was concentrated by distillation and finally under water aspirator reduced pressure, at a solution temperature of 50° C. A sample of the product was withdrawn for a purity check: purity 99+% by gas chromatography (excluding ether). The product was used in the preparation of the hydrochloride without further purification.

II. Hydrochloride Formation

The product of the preceding step was dissolved in a solution of 2.65 liters of methyl alcohol and 14.2 liters of isopropyl alcohol. Gaseous hydrogen chloride was introduced, with stirring, until the pH of the solution was lowered to 1.1–1.5. The solution was cooled slowly and finally to 0° to 5° C. The crystals were collected in a Buchner filter funnel and washed with cold isopropyl alcohol. The crystalline product was vacuum dried at 60° C. There was obtained 1163 g, m.p. 287°–288° C. (decomp.) 99+% pure. Concentration of the mother liquors to 1.5 liters on cooling gave 35 g of additional product (m.p. 286°–287° C). The filtrate was saved for further reclamation.

III. The overall yield for the combined reduction and hydrochloride preparation steps was 95% for the first crop and 2.8+% for the second crop, thus giving a total yield of 97.8%. By way of comparison, Rice, Wheeler and Geschickter reported a yield for the reduction step of the distilled liquid dione which calculated to be 84%, and gave no yield for the preparation of the hydrochloride.

To readily enable a person skilled in the art to practice the invention, seed crystals of N-(3-dimethylaminopropyl)-2-aza-8,8-diethyl-8-germaspiro[4:5]decane-1,3-dione have been deposited at the United States Pharmacopeia in Rockville, Md., where they are identified as Catalogue No. 2101, Lot F. Orders should be directed to USP-NF, Reference Standard, 12601 Twinbrook Parkway, Rockville, Md. 20852.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A dialkylgermaazaspirodione compound in crystalline form and having the formula:

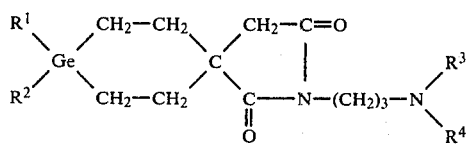

wherein $R^1$ and $R^2$ are the same or different alkyl groups of 1 to about 4 carbon atoms and $R^3$ and $R^4$ are the same or different alkyl groups of 1 to about 4 carbon atoms.

2. A crystalline composition of claim 1 having a purity in excess of 98%.

3. A crystalline composition of claim 1 having a purity in excess of 99%.

4. A crystalline composition of claim 1 having a purity in excess of 99.8%.

5. The compound N-(3-dimethylaminopropyl)-2-aza-8,8-diethyl-8-germaspiro[4:5]decane-1,3-dione in crystalline form.

6. A crystalline composition of claim 5 having a purity in excess of 99%.

7. A crystalline composition of claim 5 having a purity in excess of 99.8%.

8. Orthorhombic crystals of the compound of claim 5.

9. A process of purifying a dialkylgermaazaspirodione of the formula set forth in claim 1 which comprises crystallizing said dione in the presence or absence of a solvent and separating the resulting crystals from the mother liquor.

10. A process of purifying a dialkylgermaazaspirodione compound of the formula set forth in claim 1 which comprises initiating crystallization of said dione, in the presence or absence of a solvent, allowing said dione to crystallize further, and separating the resulting crystals from the mother liquor.

11. A process of claim 10 in which the crystallization is initiated by the addition of a seed crystal to said dialkylgermaazaspirodione.

12. A process of claim 11 in which $R^1$ and $R^2$ are ethyl and $R^3$ and $R^4$ are methyl.

13. A process of claim 9 in which a solvent is present.

14. A process of claim 12 in which a low boiling hydrocarbon solvent is present.

15. A process of claim 14 in which said low boiling hydrocarbon is pentane, hexane, heptane or a mixture thereof.

16. A process of claim 10 in which $R^1$ and $R^2$ are ethyl and $R^3$ and $R^4$ are methyl.

17. A process of claim 16 in which a solvent is present.

18. A process of claim 17 in which said solvent is a low boiling hydrocarbon.

19. A process of preparing a dialkylgermaazaspirane which comprises purifying a dialkylgermaazaspirodione compound of the formula set forth in claim 1 by crystallization, and reducing said purified dione.

20. A process of producing a dialkylgermaazaspirane salt which comprises purifying a dialkylgermaazaspirodione of the formula set forth in claim 1 by crystallization, reducing said purified dione, and preparing a salt from the reduced dione by adding an acid thereto.

21. A process of claim 20 in which said acid is hydrogen chloride and the purity of the salt obtained is at least 99%.

22. A process of claim 21 in which said hydrogen chloride is added to said dione in an alcoholic solution.

23. A process of claim 22 in which the alcohol in said alcoholic solution is methanol, ethanol, isopropanol, propanol or a mixture thereof.

24. A process of claim 20 in which $R^1$ and $R^2$ are ethyl and $R^3$ and $R^4$ are methyl.

25. A process of claim 21 in which $R^1$ and $R^2$ are ethyl and $R^3$ and $R^4$ are methyl.

26. A process of claim 22 in which $R^1$ and $R^2$ are ethyl and $R^3$ and $R^4$ are methyl.

* * * * *

UNITED STATES PATENT AND TRADEMARK OFFICE
CERTIFICATE OF CORRECTION

PATENT NO. : 4,248,785
DATED : February 3, 1981
INVENTOR(S) : Chester M. McCloskey, James R. Fischer and Leonard F. Scott It is certified that error appears in the above—identified patent and that said Letters Patent is hereby corrected as shown below:

At Column 1, line 30, after "J. Heterocyclic Chem.," change "11" to --$\underline{11}$--.

At Column 2, line 44, after the word "time" insert --much--;

line 56, change "flurochlorocar-" to --fluorochlorocar---.

At Column 3, line 54, change "ehtyl" to --ethyl--; same line, change "mixture" to --mixtures--.

Signed and Sealed this

Twenty-first Day of April 1981

[SEAL]

Attest:

RENE D. TEGTMEYER

Attesting Officer    Acting Commissioner of Patents and Trademarks